(12) United States Patent
Michel et al.

(10) Patent No.: US 8,962,865 B2
(45) Date of Patent: Feb. 24, 2015

(54) PROCESS FOR THE PREPARATION OF N-MONOSUBSTITUTED β-AMINO ALCOHOLS

(71) Applicant: Lonza AG, Basel (CH)

(72) Inventors: Dominique Michel, Sierre (CH); Rudolf Fuchs, Sitten (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 13/950,412

(22) Filed: Jul. 25, 2013

(65) Prior Publication Data

US 2013/0310574 A1    Nov. 21, 2013

Related U.S. Application Data

(60) Continuation of application No. 12/868,419, filed on Aug. 25, 2010, now Pat. No. 8,558,014, which is a continuation of application No. 12/801,231, filed on May 28, 2010, now abandoned, which is a continuation of application No. 10/520,362, filed as application No. PCT/EP03/07411 on Jul. 9, 2003, now abandoned, application No. 13/950,412, which is a continuation of application No. 12/003,752, filed on Dec. 31, 2007, now abandoned, which is a division of application No. 10/520,362, filed on Apr. 18, 2005, now abandoned.

(30) Foreign Application Priority Data

Jul. 9, 2002   (EP) .................................. 02015229

(51) Int. Cl.
```
C07D 333/16    (2006.01)
C07D 307/42    (2006.01)
C07D 307/80    (2006.01)
C07D 333/56    (2006.01)
C07D 333/20    (2006.01)
C07C 213/00    (2006.01)
C07C 221/00    (2006.01)
C07C 225/16    (2006.01)
C07D 307/46    (2006.01)
C07D 333/22    (2006.01)
C07D 307/52    (2006.01)
```
(52) U.S. Cl.
CPC ............ C07D 333/20 (2013.01); C07D 307/80 (2013.01); C07D 333/56 (2013.01); C07D 333/16 (2013.01); C07D 307/42 (2013.01); C07C 213/00 (2013.01); C07C 221/00 (2013.01); C07C 225/16 (2013.01); C07D 307/46 (2013.01); C07D 333/22 (2013.01); C07D 307/52 (2013.01)
USPC ............... 549/49; 549/75; 549/467; 549/491; 564/355

(58) Field of Classification Search
CPC .. C07D 333/16; C07D 307/42; C07D 307/80; C07D 333/56
USPC ..................... 549/49, 75, 467, 491; 564/355
See application file for complete search history.

(56) References Cited

U.S. PATENT DOCUMENTS

| | | | |
|---|---|---|---|
| 4,515,986 A | 5/1985 | Bernhagen et al. | 564/471 |
| 5,362,886 A | 11/1994 | Berglund | 549/75 |
| 5,491,243 A | 2/1996 | Berglund | 549/75 |

FOREIGN PATENT DOCUMENTS

| | | |
|---|---|---|
| EP | 0046288 | 2/1982 |
| EP | 0457559 | 11/1991 |
| EP | 0650965 | 5/1995 |
| WO | 2004/020391 A1 | 3/2004 |

OTHER PUBLICATIONS

Opposition Proceeding, Application No./Patent No. 03 762 669.4-1521/1 539 673, Decision Revoking European Patent, dated Jan. 25, 2012, 19 pages.
Opposition Proceeding, Application No. 03 762 669.4-1521/1 539 673, Summons to Attend Oral Proceedings, dated Jul. 28, 2011, 26 pages.
Romp-Lexikon Chemie, Bd. 2. CM-G., 10. Auflage, Thieme, "Druck", pp. 1046-1047.
Becker, Heinz G.O., et al., Organikum, Organisch-chemisches Grundpraktikum, Kapitel 7.2.1.5, Mannich-Reaktion, Wiley-VCH, pp. 530-532, 619 (2001).
Thompson, B. Blackburn, "The Mannich Reaction—Mechanistic and Technological Considerations," J. Pharm. Sciences, vol. 57, No. 5, pp. 715-733 (1968).
Hill, John A., et al., "Synthesis of Tritium Labelled 1-(3, 4-Dichlorophenyl)-3-(methylamino)propanol hydrochloride", Journal of Labelled Compounds and Radiopharmaceuticals, vol. XXVIII, No. 7, pp. 811-818 (1990).

(Continued)

Primary Examiner — Shawquia Jackson
(74) Attorney, Agent, or Firm — Hoffman & Baron, LLP

(57) ABSTRACT

A process is disclosed for the preparation of a compound of formula

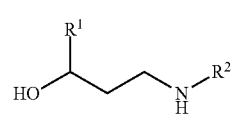

and/or an addition salt of a proton acid, wherein $R^1$ and $R^2$ independently represent alkyl, cycloalkyl, aryl or aralkyl, each aryl or aralkyl being optionally further substituted with alkyl, alkoxy and/or halogen.

8 Claims, No Drawings

(56) References Cited

OTHER PUBLICATIONS

Wheeler, William J., "Approaches to an Asymmetric Synthesis of Duloxetine, A Mixed Uptake Inhibitor of Serotonin and Norepinephrine, and its C-14 Labeled Analogs," Synthesis and Applications of Isotopically Labelled Compounds, pp. 597-603 (1994).

L.A. Sorbera, et al., "Duloxetine Oxalate," Drugs of the Future 2000, vol. 25(9); pp. 907-916 (2009).

Blicke, F.F., "The Mannich Reaction—Chapter 10", Organic Reactions, vol. I, pp. 303-341 (1942).

Liu, H., et. al., Chirality, 12 (2000), 26-29.

Deeter J., et al., Tetrahedron Lett., 31, (1990), 7101-7104.

Mannich, C., et al., Chem. Ber., 55, (1922), 356-365.

Blicke et al., J. Am. Chem. Soc., 64, (1942), 451-454.

Becker et al., Wiss. Z. Tech. Hochsch. Chem. Leuna-Merseburg, 11, (1969), 38-41.

Blicke. F.F., Organic Reactions, vol. I, (1942), pp. 303-341.

Kiyoshi Matsumoto, Angewandte Chemine., vol. 94, No. 12, (1982), p. 937.

Chemical Abstracts., vol. 56, No. 1, (1962), abstract No. 363g.

Denis, G.I., et al., Izvest. Vysshikh Ucheb. Zavedenii, Khim. I Khim. Tekhnol., vol. 4, (1961), pp. 426-428.

Chemical Abstracts, vol. 52, No. 13, (1958), abstract No. 11067b.

Nobles, Lewis, W. et al., J. Am. Pharm. Assoc., Sci. Ed., vol. 67, (1958), pp. 77-81.

Chemical Abstracts, vol. 63, No. 8, (1965), abstract 9900g.

Landl-Vittory, R., et al., Farmaco (Pavia), vol. 18, No. 2, (1965), pp. 109-118.

Chemical Abstracts, vol. 67, No. 11, (1967), abstract No. 53946c.

Chemical Abstracts, vol. 101, No. 13, (1984), abstract No. 110812c.

Saakyan, A.M., et al., Ar. Khim. Zh., vol. 37, No. 4, (1984), pp. 261-265.

Chemical Abstracts, vol. 95, No. 1. (1981), abstract No. 6707u.

Agarwal, S.K., et al., J. Indian Chem. Soc., vol. 57, No. 12, (1980), pp. 1240-1241.

Chemical Abstracts, vol. 70, No. 9, (1969), abstract No. 37630b.

Tilak, B.D., et al., Indian J. Chem., vol. 6. No. 8, (1968), pp. 422-427.

Chemical Abstracts, vol. 102, No. 1, (1985), abstract No. 6087e.

Xu, Xiujuan, et al., Huaxue Xuebao, vol. 42, No. 7, (1984), pp. 688-692.

Chemical Abstracts, vol. 59, No. 2, (1963), abstract No. 1625b.

Saldabos, N., et al., Latvijas Psr Zinatnu Akad. Vestis, Kim. Ser., vol. 2, (1962), pp. 309-310.

Lewis, W., et al., Journal of the American Pharmaceutical Association, vol. 47, No. 2, (1958, pp. 77-81.

Ardashev, B.I., et al., Khim. Geterotsikl. Soedin., vol. 1, (1967), pp. 7 to 9.

Becker et al., Wiss. Z. Tech. Hochsch. Chem. Leuna-Merseburg, 11, (1969), 38 to 41.

PROCESS FOR THE PREPARATION OF N-MONOSUBSTITUTED β-AMINO ALCOHOLS

This application is a continuation of U.S. Ser. No. 12/868,419 filed Aug. 25, 2010, which is a continuation of U.S. Ser. No. 12/801,231, filed on May 28, 2010, which is a continuation of U.S. Ser. No. 10/520,362, filed on Apr. 18, 2005, which is a section 371 national stage application of international (PCT) application no. PCT/EP03/007411, filed on Jul. 9, 2003, which has priority benefit of European patent application serial no. 02015229.4, filed on Jul. 9, 2002, and which is a continuation of U.S. Ser. No. 12/003,752, filed on Dec. 31, 2007, which is a division of U.S. Ser. No. 10/520,362, filed on Apr. 18, 2005.

The invention relates to a process for the preparation of N-monosubstituted β-amino alcohols of formula

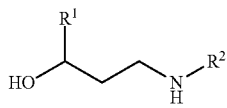

I and/or an addition salt of a proton acid via direct synthesis of N-monosubstituted β-keto amines of formula

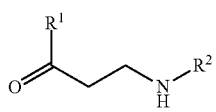

II and/or an addition salt of a proton acid.

N-Monosubstituted β-amino alcohols of formula I like (S)-(−)-3-N-methylamino-1-(2-thienyl)-1-propanol (LY293628) are useful key intermediates and building blocks for the preparation of pharmaceutically active compounds like (S)-(+)-methyl-[3-(1-naphthyloxy)-3-(2-thienyl)-propyl]-amine ((S)-duloxetine) (Liu, H. et al., *Chirality* 12 (2000) 26-29), a potential neuro-active compound which strongly inhibits the serotonine and norephedrine uptake (Deeter, J. et al., *Tetrahedron Lett.* 31 (1990) 7101-7104).

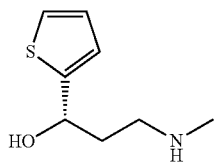

LY293628

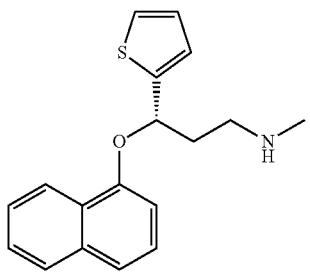

(S)-duloxetine

In the following the terms "amine" or "amines" include their corresponding addition salts of proton acids.

Direct preparation of N-monosubstituted β-keto amines of formula II establishes an alternative and economically advantageous source for industrial production of N-monosubstituted β-amino alcohols of formula I.

Compounds of formula II were first synthesized in 1922 by reacting ketones with formaldehyde and primary or secondary alkylamines in the presence of hydrochloric acid (Mannich, C. et al., *Chem. Ber.* 55 (1922) 356-365). In said reactions with primary alkylamines formation of hydrochlorides of tertiary β-keto amines of formula

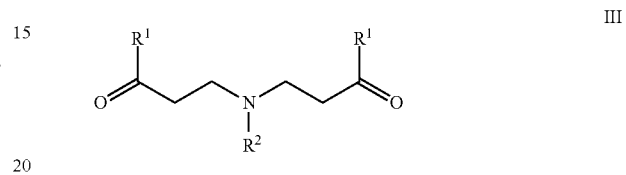

III prevails over formation of hydrochlorides of secondary β-keto amines of formula II. These findings were supported by Blicke et al. (*J. Am. Chem. Soc.* 64 (1942) 451-454) and Becker et al. (*Wiss. Z. Tech. Hochsch. Chem. Leuna-Merseburg.* 11 (1969) 38-41).

According to Mannich et al. steam destillation of tertiary β-keto amines of formula III results in formation of secondary β-keto amines of formula II in fairly satisfactory yields, accompanied by vinyl compounds and other by-products.

In spite of the loss of more than 50% of the starting compounds and due to lack of alternative processes this procedure is still used for the preparation of secondary β-keto amines.

Another drawback in presently known preparation methods of β-keto amines is the need of isolation of the desired intermediate compounds of formula II from unwanted by-products of formula III.

EP-A 457 559 and EP-A 650 965 disclose the preparation of N,N-dimethyl β-amino alcohols via Mannich-type reactions of methyl ketones with paraformaldehyde and dimethylamine followed by reduction of the carbonyl group. After reaction of the hydroxyl group affording alkyl or aryl ether derivatives one methyl radical is removed to obtain N-monosubstituted compounds which requires delicate and expensive reactions.

Only Becker et al. disclose some few examples with yields of about 60% of N-monomethyl β-keto amines using N-methylammonium oxalates as nitrogen source. Nevertheless, the process disclosed by Becker et al. is not advantageous because it strictly depends on the use of amino oxalates. In contrast to the free amines or corresponding hydrochlorides oxalates of primary amines are not commercially available and their preparation requires further synthesis and purification steps.

Using oxalates is also disadvantageous because it requires additional reduction equivalents in the next step, reducing the ketone intermediates to the title compounds.

None of the known processes for the production of N-monosubstituted β-amino alcohols of formula I and ether derivatives thereof includes, intends or concerns intermediate products comparable to N-monosubstituted β-keto amines of formula II of the present invention. Although still many efforts were made to find new preparation processes, the pathway of the present invention for direct synthesis of N-monosubstituted β-keto amines and subsequent reduction to N-monosubstituted β-amino alcohols is not yet disclosed.

The problem to be solved was to provide an alternative and efficient process for the synthesis of N-monosubstituted β-amino alcohols and derivatives thereof in high yields. Furthermore, the proposed process should provide high yields independently of steric aspects of the used amino or carbonyl compounds.

The problems mentioned above could be solved according to claim 1.

Starting with commercially available methyl ketones and primary amines and/or an addition salt of a proton acid, which were reacted with formaldehyde in the presence a solvent and optionally of a proton acid at a pressure above 1.5 bar N-monosubstituted β-amino ketones which could be directly reduced to the desired N-monosubstituted β-amino alcohols were obtained in high yields.

As a further advantage of the instant process high yields of N-monomethyl β-amino ketones can be obtained by direct usage of methylamine hydrochloride which is easily available, cheap and, since it is a solid compound, easy to handle.

The present invention discloses a process for the preparation of a compound of formula

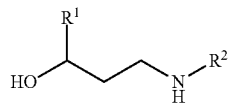

I and/or an addition salt of a proton acid, wherein $R^1$ and $R^2$ independently represent alkyl, cycloalkyl, aryl or aralkyl, each being optionally further substituted with alkyl, alkoxy and/or halogen, which process comprises the steps of
a) reacting a mixture comprising
  (i) a methyl ketone of formula

IV wherein $R^1$ is as defined above,
  (ii) a compound of formula

  $H_2N$—$R^2$

V and/or an addition salt of a proton acid, wherein $R^2$ is as defined above, and
  (iii) formaldehyde or a source of formaldehyde selected from the group consisting of formaldehyde in aqueous solution, 1,3,5-trioxane, paraformaldehyde and mixtures thereof, in the presence of
  a solvent selected from the group consisting of water, aliphatic alcohols, cycloaliphatic alcohols and mixtures thereof, and
  optionally a proton acid
to afford a compound of formula

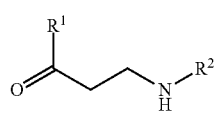

II and/or an addition salt of a proton acid, and
b) reducing the carbonyl group of said β-amino ketone to afford a compound of formula I, and/or an addition salt of a proton acid, wherein the first step is carried out at a pressure above 1.5 bar.

In a preferred embodiment $R^1$ and $R^2$ can independently represent linear or branched $C_{1-8}$ alkyl, $C_{3-8}$ cycloalkyl, phenyl, naphthyl, furanyl, benzofuranyl, thienyl, benzo[b]thienyl or aralkyl, wherein the alkyl moiety of the aralkyl residue is linear $C_{1-4}$ alkyl, and the aryl moiety is selected from the group consisting of phenyl, naphthyl, furanyl, benzofuranyl, thienyl and benzo[b]thienyl,
each aryl or aralkyl being optionally substituted with halogen, linear or branched $C_{1-4}$ alkyl, linear or branched $C_{1-4}$ alkoxy, $C_{3-6}$ cycloalkyl, $CF_3$, $C_2F_5$, $OCF_3$ or $OC_2F_5$.

It is particularly preferred that $R^1$ represents furanyl or thienyl.

It is also particularly preferred that $R^2$ represents linear or branched $C_{1-8}$ alkyl. More particularly preferred $R^2$ represents methyl, ethyl, propyl, isopropyl, butyl, isobutyl or ten-butyl.

Preferably, the compound of formula V is used as a free amine and/or an addition salt of a proton acid. Particularly preferred are free amines, formates, acetates, oxalates, hydrochlorides, hydrobromides or mixtures thereof. More particularly preferred are free amines and/or hydrochlorides.

In a preferred embodiment the compound of formula V is present in an amount at least equimolar to that of the compound of formula IV. Particularly preferred the molar ratio of the compound of formula V to the compound of formula IV is between 1 and 2.

In a preferred embodiment the solvent comprises water, an aliphatic or cycloaliphatic alcohol or a mixture thereof.

Particularly preferred alcohols are linear or branched aliphatic $C_{1-12}$ alcohols, cycloaliphatic $C_{5-8}$ alcohols, di- and/or trimeric ethylene glycols or mono $C_{1-4}$ alkyl or acetyl derivatives thereof, each of said alcohols containing 1 to 3 hydroxy groups.

Examples for said alcohols are methanol, ethanol, propanol, isopropyl alcohol, butanol, isobutanol, tert-butanol, 2-butanol, 1-pentanol, 2-pentanol, 3-pentanol, 1-hexanol, 2-hexanol, cyclopentanol, cyclohexanol, 1,2-ethanediol, 1,2-propanediol, 1,2-butanediol, 2,3-butanediol, 1,4-butanediol, 1,2,3-propanetriol, 1,2,6-hexanetriol, diethylene glycol, diethylene glycol monomethyl ether, diethylene glycol monoethyl ether, diethylene glycol monobutyl ether, diethylene glycol monoacetate, triethylene glycol, triethylene glycol monomethyl ether, triethylene glycol monoethyl ether, triethylene glycol monobutyl ether and triethylene glycol monoacetate.

Preferably said alcohol is ethanol, propanol, isopropyl alcohol, butanol, isobutanol, tert-butanol, diethylene glycol or triethylene glycol.

The proton acid can be any organic or inorganic acid, the acid being preferably selected from the group consisting of formic acid, acetic acid, propionic acid, oxalic acid, malonic acid, benzoic acid, HF, HCl, HBr, HI, $H_2SO_4$ and $H_3PO_4$. In a preferred embodiment the proton acid can be an acidic salt of a polybasic organic or inorganic acid like monoalkali malonates, alkali hydrogensulfates, alkali hydrogenphosphates and alkali hydrogencarbonates.

More preferably the proton acid is selected from the group consisting of formic acid, acetic acid, propionic acid, oxalic acid, HCl and HBr, more preferably it is selected from the group consisting of formic acid, acetic acid, HCl and HBr.

Preferably reaction step a) is carried out either with added addition salts of amines or proton acids, since even distilled free β-amino ketones of formula II tend to decompose and form by-products while stored, whereas the corresponding additions salts can be stored over a longer period without decomposition. In the products, the ratio of free amine and its salt corresponds to the ratio of added addition salts of amines and proton acids to the whole amine amount during reaction step a).

In a preferred embodiment the pressure during reaction step a) is above 1.5 bar, more preferably in the range of 1.5 to 10 bar and particularly preferred in the range of 1.5 to 5 bar.

In contrast to Becker et al. the inventive process generally allows direct preparation of N-monosubstituted β-keto amines and addition salts of proton acids thereof. The products obtained by the inventive process can be reduced or subsequently reacted without further conversion into other salts.

The present invention also provides a compound of formula

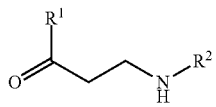

II and its addition salts of proton acids,
wherein $R^1$ represents furanyl, benzofuranyl, isobenzofuranyl, thienyl or benzo[b]thienyl, each being optionally substituted with halogen, linear or branched $C_{1-4}$ alkyl, linear or branched $C_{1-4}$ alkoxy, $C_{3-6}$ cycloalkyl, $CF_3$, $C_2F_5$, $OCF_3$ or $OC_2F_5$, and
wherein $R^2$ is selected from the group consisting of linear or branched $C_{1-8}$ alkyl, $C_{3-8}$ cyclo-alkyl, phenyl, naphthyl, furanyl, benzofuranyl, thienyl, benzo[b]thienyl and aralkyl, wherein the alkyl moiety of the aralkyl residue is linear $C_{1-4}$ alkyl, and the aryl moiety is selected from the group consisting of phenyl, furanyl, benzofuranyl, thienyl and benzo[b]thienyl,
each aryl or aralkyl being optionally substituted with halogen, linear or branched $C_{1-4}$ alkyl, linear or branched $C_{1-4}$ alkoxy, $C_{3-6}$ cycloalkyl, $CF_3$, $C_2F_5$, $OCF_3$ or $OC_2F_5$,
with the exception of the compound wherein $R^1$ is thienyl and $R^2$ is benzyl.

The present invention also provides a compound of formula

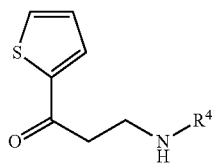

VI and its addition salts of proton acids, wherein $R^4$ represents methyl, ethyl, isobutyl and tert-butyl.

The present invention also provides a compound of formula

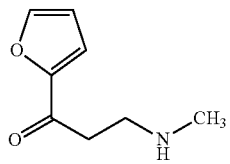

VII and its addition salts of proton acids.

The present invention also provides a compound of formula

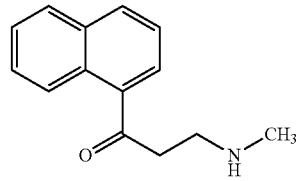

VIII and its addition salts of proton acids.

The present invention also provides a process for the preparation of a compound of formula

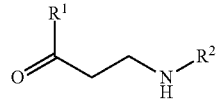

II and/or an addition salt of a proton acid, wherein $R^1$ and $R^2$ independently represent alkyl, cycloalkyl, aryl or aralkyl, each being optionally further substituted with alkyl, alkoxy and/or halogen,
which process comprises reacting a mixture comprising
(i) a methyl ketone of formula

IV wherein $R^1$ is as defined above, and
(ii) a compound of formula

$$H_2N—R^2$$

V and/or an addition salt of a proton acid, wherein $R^2$ is as defined above, and
(iii) formaldehyde or a source of formaldehyde selected from the group consisting of formaldehyde in aqueous solution, 1,3,5-trioxane, paraformaldehyde and mixtures thereof, in the presence of
a solvent selected from the group consisting of water, aliphatic alcohols, cycloaliphatic alcohols and mixtures thereof, and
optionally a proton acid
to afford a compound of formula

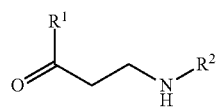

II and/or an addition salt of a proton acid, wherein $R^1$ and $R^2$ are as defined above, and wherein the reaction is carried out at a pressure above 1.5 bar.

In a preferred embodiment $R^1$ and $R^2$ independently represent linear or branched $C_{1-8}$ alkyl, $C_{3-8}$ cycloalkyl, phenyl, naphthyl, furanyl, benzofuranyl, thienyl, benzo[b]thienyl and aralkyl, wherein the alkyl moiety of the aralkyl residue is linear $C_{1-4}$ alkyl, and the aryl moiety is selected from the group consisting of phenyl, naphthyl, furanyl, benzofuranyl, thienyl and benzo[b]thienyl, each aryl or aralkyl being optionally substituted with halogen, linear or branched $C_{1-4}$ alkyl, linear or branched $C_{1-4}$ alkoxy, $C_{3-6}$ cycloalkyl, $CF_3$, $C_2F_5$, $OCF_3$ or $OC_2F_5$.

It is particularly preferred that $R^1$ represents furanyl or thienyl. It is also particularly preferred that $R^2$ represents linear or branched $C_{1-8}$ alkyl. More particularly preferred $R^2$ represents methyl, ethyl, propyl, isopropyl, butyl, isobutyl or tert-butyl.

Preferably, the compound of formula V can be used as a free amine and/or an addition salt of a proton acid thereof. Particularly preferred are free amines, formates, acetates, oxalates, hydrochlorides, hydrobromides or mixtures thereof. More particularly preferred are free amines and/or hydrochlorides.

In one preferred embodiment the compound of formula V is present in an amount at least equimolar to that of the compound of formula IV. Particularly preferred the molar ratio of the compound of formula V to the compound of formula IV is between 1 and 2.

In a preferred embodiment the solvent comprises water, an aliphatic or cycloaliphatic alcohol or a mixture thereof.

Particularly preferred alcohols are linear or branched aliphatic $C_{1-12}$ alcohols, cycloaliphatic $C_{5-8}$ alcohols, di- and/or trimeric ethylene glycols or mono $C_{1-4}$ alkyl or acetyl derivatives thereof, each of said alcohols containing 1 to 3 hydroxy groups.

Examples for said alcohols are methanol, ethanol, propanol, isopropyl alcohol, butanol, isobutanol, tert-butanol, 2-butanol, 1-pentanol, 2-pentanol, 3-pentanol, 1-hexanol, 2-hexanol, cyclopentanol, cyclohexanol, 1,2-ethanediol, 1,2-propanediol, 1,2-butanediol, 2,3-butanediol, 1,4-butanediol, 1,2,3-propanetriol, 1,2,6-hexanetriol, diethylene glycol, diethylene glycol monomethyl ether, diethylene glycol monoethyl ether, diethylene glycol monobutyl ether, diethylene glycol monoacetate, triethylene glycol, triethylene glycol monomethyl ether, triethylene glycol monoethyl ether, triethylene glycol monobutyl ether and triethylene glycol monoacetate.

Preferably said alcohol is ethanol, propanol, isopropyl alcohol, butanol, isobutanol, tert-butanol, diethylene glycol or triethylene glycol.

The proton acid can be any organic or inorganic acid, the acid being preferably selected from the group consisting of formic acid, acetic acid, propionic acid, oxalic acid, malonic acid, benzoic acid, HF, HCl, HBr, HI, $H_2SO_4$ and $H_3PO_4$. In a preferred embodiment the proton acid is an acidic salt of a polybasic organic or inorganic acids like monoalkali malonates, alkali hydrogensulfates, alkali hydrogenphosphates and alkali hydrogencarbonates. More preferably the proton acid is selected from the group consisting of formic acid, acetic acid, propionic acid, oxalic acid, HCl and HBr, more preferably it is selected from the group consisting of formic acid, acetic acid, HCl and HBr.

In a preferred embodiment the pressure during the reaction is above 1.5 bar, more preferably in the range of 1.5 to 10 bar and particularly preferred in the range of 1.5 to 5 bar.

The present invention is illustrated by the following non-limiting examples.

General Procedure for Examples 1 to 8

A mixture of methyl ketone (1 equivalent (eq)), primary alkyl amine and/or an addition salt thereof (1.1 to 1.5 eq), formaldehyde (1.4 to 1.5 eq), a solvent, optionally in the presence of a proton acid, is heated in an autoclave at a total pressure above 1.5 bar for 5 to 24 hours. Afterwards, the reaction solution is cooled to 20° C. Optionally the reaction solvent can than be removed partly or in whole and a solvent like ethyl acetate or isopropyl alcohol can be added under vigorous stirring, if necessary to facilitate precipitation of the product. The suspension is cooled (0 to 20° C.) and filtered after precipitation (0.5 to 10 hours), optionally washed and dried to afford a slightly yellow to white powder in a yield between 50 and 75%. The product can be recrystallized from isopropyl alcohol and/or ethyl acetate if necessary. If the stability of the free base is sufficient at ambient conditions, extracting with an organic solvent and an aqueous base affords the free base.

General Procedure for Comparative Examples 1 to 6

A mixture of methyl ketone (1 eq), primary alkyl amine and/or an addition salt thereof (1 to 1.5 eq), formaldehyde (1.0 to 1.5 eq), optionally in the presence of a proton acid, is heated in refluxing solvent for 5 to 24 hours. Afterwards, the mixture is cooled to 20° C. Optionally the reaction solvent can than be removed partly or in whole and a solvent like ethyl acetate or isopropyl alcohol can be added under vigorous stirring, if necessary to facilitate precipitation of the product. The suspension is cooled (0 to 20° C.) and filtered after precipitation (0.5 to 10 hours), optionally washed and dried to afford a slightly yellow to white powder in a yield between 30 and 45%. The product can be recrystallized from isopropyl alcohol and/or ethyl acetate if necessary.

EXAMPLE 1

3-(Methylamino)-1-(thiophen-2-yl)propan-1-one hydrochloride (II, $R^1$=thiophen-2-yl, $R^2$=methyl)

2-Acetylthiophene (25.5 g, 200 mmol); methylamine hydrochloride (14.9 g, 220 mmol, 1.1 eq); paraformaldehyde (8.2 g, 280 mmol, 1.4 eq); HCl conc. (1.0 g); ethanol (100 mL); 110° C. for 9 hours; ca. 2 to 2.5 bar; removing of ethanol (50 mL) in vacuo; addition of ethyl acetate (200 mL); ca. 71% yield.

$^1$H-NMR δ (DMSO-$d_6$, 400 MHz): 9.16 (2H, s, br), 8.07 (1H, dd, J=5.0, 1.0), 8.01 (1H, dd, J=3.8, 1.0), 7.29 (1H, dd, J=5.0, 3.8), 3.49 (2H, t), 3.20 (2H, t), 2.56 (3H, s).

$^{13}$C-NMR δ (DMSO-$d_6$, 100 MHz): 189.9, 142.7, 135.4, 133.8, 128.8, 43.1, 34.6, 32.4.

EXAMPLE 2

3-(Methylamino)-1-(thiophen-2-yl)propan-1-one hydrochloride (II, $R^1$=thiophen-2-yl, $R^2$=methyl)

2-Acetylthiophene (24.9 g, 197 mmol); methylamine hydrochloride (14.8 g, 219 mmol, 1.1 eq); paraformaldehyde (8.3 g, 276 mmol, 1.4 eq); HCl conc. (1.1 g); isopropyl alcohol (100 mL); 110° C. for 8 hours; ca. 2 to 2.5 bar; addition of isopropyl alcohol (50 mL); ca. 65% yield.

COMPARATIVE EXAMPLE 1

3-(Methylamino)-1-(thiophen-2-yl)propan-1-one hydrochloride (II, $R^1$=thiophen-2-yl, $R^2$=methyl)

2-Acetylthiophene (7.9 g, 300 mmol); methylamine hydrochloride (30.4 g, 450 mmol, 1.5 eq); paraformaldehyde (12.6 g, 420 mmol, 1.4 eq); HCl conc. (1.5 g); isopropyl alcohol (200 mL); heating under reflux (82° C.) for 8 hours; addition of ethyl acetate (200 mL); ca. 43% yield.

EXAMPLE 3

3-(Ethylamino)-1-(thiophen-2-yl)propan-1-one hydrochloride (II, $R^1$=thiophen-2-yl, $R^2$=ethyl)

2-Acetylthiophene (6.3 g, 50 mmol); ethylamine hydrochloride (6.1 g, 75 mmol, 1.5 eq); paraformaldehyde (2.1 g, 75 mmol, 1.5 eq); HCl conc. (0.3 g); ethanol (35 mL); 110° C. for 9 hours; ca. 2 to 2.5 bar; removing of ethanol (25 mL) in vacuo; addition of ethyl acetate (50 mL); ca. 73% yield.
$^1$H-NMR δ (DMSO-$d_6$, 400 MHz): 9.3 (2H, s, br), 8.08 (1H, dd), 8.00 (1H, dd), 7.28 (1H, dd), 3.51 (2H, t), 3.20 (2H, t), 2.96 (2H, q), 1.23 (3H, t).

COMPARATIVE EXAMPLE 2

3-(Ethylamino)-1-(thiophen-2-yl)propan-1-one hydrochloride (II, $R^1$=thiophen-2-yl, $R^2$=ethyl)

2-Acetylthiophene (12.6 g, 100 mmol); ethylamine hydrochloride (12.2 g, 150 mmol, 1.5 eq); paraformaldehyde (4.1 g, 140 mmol, 1.4 eq); HCl conc. (0.5 g); ethanol (70 mL); heating under reflux (78° C.) for 6 hours; removing of ethanol (25 mL) in vacuo; addition of ethyl acetate (70 mL); ca. 31% yield.

EXAMPLE 4

3-(Isobutylamino)-1-(thiophen-2-yl)propan-1-one hydrochloride (II, $R^1$=thiophen-2-yl, $R^2$=isobutyl)

2-Acetylthiophene (6.3 g, 50 mmol); isobutylamine hydrochloride (8.3 g, 75 mmol, 1.5 eq); paraformaldehyde (2.1 g, 75 mmol, 1.5 eq); HCl conc. (0.3 g); ethanol (35 mL); 110° C. for 9 hours; ca. 2 to 2.5 bar; removing of ethanol (35 mL) in vacuo; addition of ethyl acetate (50 mL); ca. 56% yield.
$^1$H-NMR δ (DMSO-$d_6$, 400 MHz): 9.0 (2H, s, br), 8.08 (1H, dd), 7.99 (1H, dd), 7.29 (1H, dd), 3.55 (2H, t), 3.22 (2H, t), 2.78 (2H, d), 2.03 (1H, m), 0.96 (6H, d).

COMPARATIVE EXAMPLE 3

3-(Isobutylamino)-1-(thiophen-2-yl)propan-1-one hydrochloride (II, $R^1$=thiophen-2-yl, $R^2$=isobutyl)

2-Acetylthiophene (12.6 g, 100 mmol); isobutylamine hydrochloride (16.5 g, 150 mmol, 1.5 eq); paraformaldehyde (4.1 g, 140 mmol, 1.4 eq); HCl conc. (0.5 g); butanol (70 mL); heating under reflux (108° C.) for 7 hours; addition of ethyl acetate (100 mL); ca. 40% yield.

EXAMPLE 5

3-(tert-Butylamino)-1-(thiophen-2-yl)propan-1-one hydrochloride (II, $R^1$=thiophen-2-yl, $R^2$=tert-butyl)

2-Acetylthiophene (6.3 g, 50 mmol); tert-butylamine hydrochloride (8.3 g, 75 mmol, 1.5 eq); paraformaldehyde (2.1 g, 75 mmol, 1.5 eq); HCl conc. (0.3 g); butanol (35 mL); 117° C. for 9 hours; ca. 2 to 2.5 bar; addition of ethyl acetate (50 mL); ca. 52% yield.
$^1$H-NMR δ (DMSO-$d_6$, 400 MHz): 9.2 (2H, s, br), 8.08 (1H, dd), 7.98 (1H, dd), 7.30 (1H, dd), 3.54 (2H, t), 3.19 (2H, t), 1.34 (9H, s).

COMPARATIVE EXAMPLE 4

3-(tert-Butylamino)-1-(thiophen-2-yl)propan-1-one hydrochloride (II, $R^1$=thiophen-2-yl, $R^2$=tert-butyl)

2-Acetylthiophene (12.6 g, 100 mmol); tert-butylamine hydrochloride (16.5 g, 150 mmol, 1.5 eq); paraformaldehyde (4.1 g, 140 mmol, 1.4 eq); HCl conc. (0.5 g); butanol (70 mL); heating under reflux (108° C.) for 18 hours; addition of ethyl acetate (100 mL); ca. 37% yield.

EXAMPLE 6

3-(Methylamino)-1-(furan-2-yl)propan-1-one hydrochloride (II, $R^1$=furan-2-yl, $R^2$=methyl)

2-Acetylfuran (7.5 g, 68 mmol); methylamine hydrochloride (6.9 g, 102 mmol, 1.5 eq); paraformaldehyde (3.1 g, 102 mmol, 1.5 eq); HCl conc. (1.15 g); ethanol (35 mL); 110° C. for 8 hours; ca. 2 to 2.5 bar; removing of ethanol (30 mL) in vacuo; addition of ethyl acetate (50 mL); ca. 64% yield.
$^1$H-NMR δ (DMSO-$d_6$, 400 MHz): 9.0 (2H, s, br), 8.05 (1H, m), 7.53 (1H, m), 6.77 (1H, m), 3.34 (2H, t), 3.2 (2H, m), 2.57 (3H, s, br).

COMPARATIVE EXAMPLE 5

3-(Methylamino)-1-(furan-2-yl)propan-1-one hydrochloride (II, $R^1$=furan-2-yl, $R^2$=methyl)

2-Acetylfuran (11.0 g, 100 mmol); methylamine hydrochloride (10.1 g, 150 mmol, 1.5 eq); paraformaldehyde (4.1 g, 140 mmol, 1.4 eq); HCl conc. (0.5 g); butanol (70 mL); heating under reflux (108° C.) for 7 hours; addition of ethyl acetate (100 mL); ca. 44% yield.

EXAMPLE 7

3-(Methylamino)-1-phenylpropan-1-one hydrochloride (II, $R^1$=phenyl, $R^2$=methyl)

2-Acetophenone (21.0 g, 175 mmol); methylamine hydrochloride (17.5 g, 263 mmol, 1.5 eq); paraformaldehyde (7.9 g, 263 mmol, 1.5 eq); HCl conc. (1.1 g); ethanol (130 mL); 115° C. for 24 hours; ca. 2 to 2.5 bar; addition of ethyl acetate (170 mL); ca. 52% yield.
$^1$H-NMR δ (DMSO-$d_6$, 400 MHz): 9.2 (2H, s, br), 8.0 (2H, m), 7.7 (1H, m), 7.6 (2H, m), 3.55 (2H, t), 3.21 (2H, t), 2.59 (3H, s).

EXAMPLE 8

3-(Methylamino)-1-(2-naphthyl)propan-1-one hydrochloride (II, $R^1$=2-naphthyl, $R^2$=methyl)

2-Acetonaphtone (8.5 g, 50 mmol); methylamine hydrochloride (5.1 g, 75 mmol, 1.5 eq); paraformaldehyde (2.1 g, 75 mmol, 1.5 eq); HCl conc. (0.3 g); ethanol (35 mL); 117° C. for 14 hours; ca. 2 to 2.5 bar; removing of ethanol (35 mL) in vacuo; addition of ethyl acetate (50 mL); ca. 60% yield.
$^1$H-NMR δ (DMSO-$d_6$, 400 MHz): 9.3 (2H, s, br), 8.74 (1H, s), 8.17 (1H, d), 8.0 (3H, m), 7.7 (2H, m), 3.70 (2H, t), 3.28 (2H, m), 2.60 (3H, s).

COMPARATIVE EXAMPLE 6

3-(Methylamino)-1-(2-naphthyl)propan-1-one hydrochloride (II, $R^1$=2-naphthyl, $R^2$=methyl)

2-Acetonaphtone (17.0 g, 100 mmol); methylamine hydrochloride (10.1 g, 150 mmol, 1.5 eq); paraformaldehyde (4.1 g, 140 mmol, 1.4 eq); HCl conc. (0.5 g); ethanol (70 mL); heating under reflux (78° C.) for 5 hours; removing of ethanol (30 mL) in vacuo; addition of ethyl acetate (100 mL); ca. 42% yield.

EXAMPLE 9

3-(Methylamino)-1-(thiophen-2-yl)propan-1-ol (I, $R^1$=thiophen-2-yl, $R^2$=methyl)

To a mixture of 3-(methylamino)-1-(thiophen-2-yl)propan-1-one hydrochloride (10.3 g, 50 mmol) and ethanol (35 mL) at 4° C. sodium hydroxide (4.0 g of a 50% aqueous solution) was added in about 5 minutes. Afterwards, neat sodium borhydride (0.95 g, 25 mmol, 1.0 eq) was added in several portions in about 30 minutes. At the end of the addition, the suspension was stirred for 4 h at the same temperature, then acetone (10.0 mL) was added dropwise in 5 minutes and the mixture was stirred for 10 additional minutes. Water (20 mL) was then added. Afterwards, the mixture was concentrated about 5 times under vacuum and the residue was extracted with tert-butyl methyl ether (2×20 mL). The collected organic phases were finally concentrated under vacuum affording an orange oil which crystallised spontaneously after a few hours. Finally, an orange solid was obtained (7.2 g, 84% yield). This compound can then be used without further purification.

$^1$H-NMR δ (DMSO-$d_6$, 400 MHz): 7.35 (1H, dd, J=4.8, 1.0), 6.94 (1H, dd, J=4.8, 3.6), 6.90 (1H, dd, J=3.6, 1.0), 4.90 (1H, t), 3.7 (2H, m), 2.56 (2H, m), 2.25 (3H, s), 1.79 (2H, q).

$^{13}$C-NMR δ (DMSO-$d_6$, 100 MHz): 150.9, 126.3, 123.7, 122.3, 67.8, 48.5, 38.7, 36.0.

EXAMPLE 10

3-(Isobutylamino)-1-(thiophen-2-yl)propan-1-ol (I, $R^1$=thiophen-2-yl, $R^2$=methyl)

To a mixture of 3-(isobutylamino)-1-(thiophen-2-yl)propan-1-one hydrochloride (4.2 g, 19.4 mmol) and ethanol (10 mL) at 4° C. sodium hydroxide (1.6 g of a 50% aqueous solution) was added in about 20 minutes. Afterwards, neat sodium borhydride (0.37 g, 9.7 mmol, 1.0 eq) was added in several portions in about 30 minutes. At the end of the addition, the suspension was stirred for 4 h at the same temperature, then acetone (10.0 mL) was added dropwise in 20 minutes and the mixture was stirred for 10 additional minutes. Afterwards the precipitate was removed by filtration and the mixture was concentrated under vacuum affording an orange oil. The crude product was purified by column chromatography using a 40:10:1 (v:v:v) mixture of methylene chloride/methanol/ammonium hydroxide (25% aqueous solution) affording 3.1 g (76% yield) of product.

$^1$H-NMR δ (DMSO-$d_6$, 400 MHz): 7.20 (1H, dd, J=4.8, 1.0), 6.98 (1H, dd), 6.94 (1H, dd, J=4.8, 3.6), 5.20 (1H, dd), 4.98 (2H, br), 3.02 (1H, m), 2.93 (1H, m), 2.43 (2H, symm. m), 2.03 (1H, m), 1.97 (1H, m), 1.80 (1H, sept), 0.95 (6H, d).

$^{13}$C-NMR δ (DMSO-$d_6$, 100 MHz): 150.9, 126.3, 123.8, 122.5, 72.1, 57.8, 48.5, 37.4, 28.2, 20.8.

The invention claimed is:

1. A process for the preparation of a compound of formula

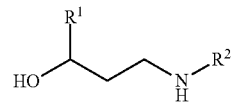

I or an addition salt of a proton acid, wherein $R^1$ is selected from the group consisting of phenyl, naphthyl, furanyl, benzofuranyl, thienyl, and benzo[b]thienyl and wherein $R^2$ is selected from the group consisting of linear or branched $C_{1-8}$ alkyl, which process comprises the following steps a) reacting a mixture comprising
(i) a methyl ketone of formula

IV wherein $R^1$ is as defined above, and
(ii) a compound of formula $H_2N—R^2$ (V)

or an addition salt of a proton acid, wherein $R^2$ is as defined above, and
(iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, propanol, isopropyl alcohol, butanol, isobutanol, tert-butanol, 2-butanol and mixtures thereof, and optionally a proton acid to afford a β-amino ketone of formula

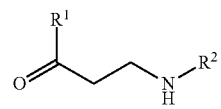

II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

2. A process for the preparation of a compound of formula

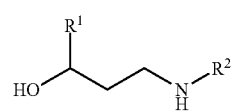

I or an addition salt of a proton acid, wherein $R^1$ is selected from the group consisting of furanyl and thienyl and wherein $R^2$ is selected from the group consisting of linear or branched $C_{1-8}$ alkyl, which process comprises the following steps a) reacting a mixture comprising
   (i) a methyl ketone of formula

                                          IV wherein R¹ is as defined above, and
   (ii) a compound of formula

 H₂N—R²                                (V)

or an addition salt of a proton acid, wherein R² is as defined above, and
   (iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, propanol, isopropyl alcohol, butanol, isobutanol, tert-butanol, 2-butanol and mixtures thereof, and optionally a proton acid to afford a β-amino ketone of formula

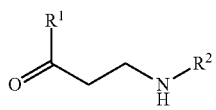                                          II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

3. A process for the preparation of a compound of formula

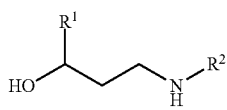                                          I or an addition salt of a proton acid, wherein R¹ is selected from the group consisting of furanyl and thienyl and wherein R² is selected from the group consisting of methyl, ethyl, propyl, isopropyl, butyl, isobutyl, or tert-butyl, which process comprises the following steps
a) reacting a mixture comprising
   (i) a methyl ketone of formula

                                          IV wherein R¹ is as defined above, and
   (ii) a compound of formula

 H₂N—R²                                (V)

or an addition salt of a proton acid, wherein R² is as defined above, and
   (iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, propanol, isopropyl alcohol, butanol, isobutanol, tert-butanol, and 2-butanol and mixtures thereof, and
   optionally a proton acid to afford a β-amino ketone of formula

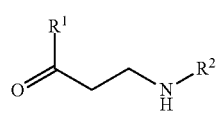                                          II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

4. A process for the preparation of a compound of formula

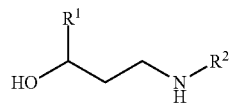                                          I or an addition salt of a proton acid, wherein R¹ is phenyl and R² is methyl, which process comprises the following steps
a) reacting a mixture comprising
   (i) a methyl ketone of formula

                                          IV wherein R¹ is as defined above, and
   (ii) a compound of formula

 H₂N—R²                               (V)

or an addition salt of a proton acid, wherein R² is as defined above, and
   (iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, isopropanol and mixtures thereof, and optionally a proton acid to afford a β-amino ketone of formula

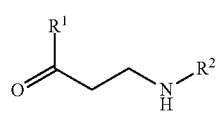                                         II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

5. A process for the preparation of a compound of formula

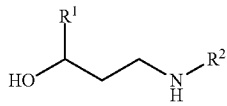

I or an addition salt of a proton acid, wherein R¹ is selected from the group consisting of furanyl and thienyl and wherein R² is selected from the group consisting of methyl, ethyl, propyl, isopropyl, butyl, isobutyl, or tert-butyl, which process comprises the following steps
a) reacting a mixture comprising
(i) a methyl ketone of formula

IV wherein R¹ is as defined above, and
(ii) a compound of formula $H_2N-R^2$ (V)

or an addition salt of a proton acid, wherein R² is as defined above, and
(iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, propanyl, isopropanol alcohol, butanol, isobutanol, tert-butanol, and 2-butanol and mixtures thereof, and optionally a proton acid to afford a β-amino ketone of formula

II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

6. A process for the preparation of a compound of formula

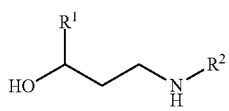

I or an addition salt of a proton acid, wherein R¹ is furanyl and R² is methyl, which process comprises the following steps
a) reacting a mixture comprising
(i) a methyl ketone of formula

IV wherein R¹ is as defined above, and
(ii) a compound of formula $H_2N-R^2$ (V)

or an addition salt of a proton acid, wherein R² is as defined above, and
(iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, isopropanol and mixtures thereof, and optionally a proton acid to afford a β-amino ketone of formula

II or an addition salt of a proton acid, and
b) reducing the carbonyl group of said β-amino ketone to afford a compound of formula I, or an addition salt of a proton acid wherein the first step is carried out by heating the mixture to a pressure above 1.5 bar.

7. A process for the preparation of a β-amino ketone of formula

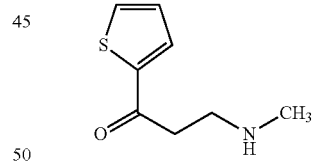

VI and its addition salts of a proton acid, which process comprises
heating to a pressure above 1.5 bar a mixture comprising
(i) a methyl ketone of formula

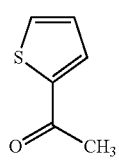

(ii) a compound of formula $H_2N-CH_3$ (V)

or an addition salt of a proton acid, and
(iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, isopropanol and mixtures thereof, and optionally a proton acid to afford a β-amino ketone of formula

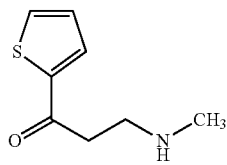

VI or an addition salt of a proton acid.

8. A process for the preparation of a β-amino ketone of formula

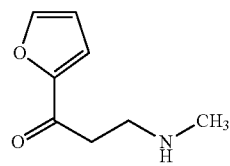

VII and its addition salts of a proton acid, which process comprises heating to a pressure above 1.5 bar a mixture comprising
(i) a methyl ketone of formula

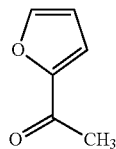

(ii) a compound of formula

    V or an addition salt of a proton acid, and
(iii) formaldehyde or a source of formaldehyde selected from the group consisting of formaldehyde in aqueous solution, 1,3,5-trioxane, paraformaldehyde and mixtures thereof, in the presence of a solvent selected from the group consisting of methanol, ethanol, isopropanol and mixtures thereof, and optionally a proton acid to afford a β-amino ketone of formula

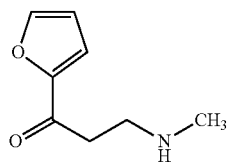

VII or an addition salt of a proton acid.

\* \* \* \* \*